United States Patent [19]

Weischedel

[11] 4,270,088
[45] May 26, 1981

[54] METHOD AND APPARATUS FOR MAGNETICALLY TESTING METAL TAPES

[75] Inventor: Herbert R. Weischedel, South Windsor, Conn.

[73] Assignee: Otis Elevator Company, Hartford, Conn.

[21] Appl. No.: 13,657

[22] Filed: Feb. 21, 1979

[51] Int. Cl.³ .................. G01N 27/82; G01R 33/12
[52] U.S. Cl. .................................. 324/241; 324/242
[58] Field of Search ............ 324/200, 225, 228, 234, 324/238–243, 217, 218

[56] References Cited

U.S. PATENT DOCUMENTS

| 2,102,452 | 12/1937 | Zuschlag | 324/241 |
| 2,855,564 | 10/1958 | Irwim et al. | 324/242 |
| 2,882,488 | 4/1959 | Price et al. | 324/225 |
| 3,328,681 | 6/1967 | Wood | 324/225 |

Primary Examiner—Gerard R. Strecker
Assistant Examiner—Walter E. Snow
Attorney, Agent, or Firm—Robert E. Greenstien

[57] ABSTRACT

Magnetic flux is induced in the tape by applying a magnetic field to the tape. Where there is a perforation or a crack air gaps are created and magnetic flux radiates outwardly from the tape across these air gaps. The presence of the crack is detected by sensing the radiating flux at two distances from the tape. At one distance, close to the tape, the total flux is the sum of the flux from the crack and the perforation. At the other distance, further from the tape, the flux is solely that produced by the perforation. A coil is placed at each position to sense the flux. The tape is moved, which causes the flux to intersect the coils. The intersection produces an output signal from each coil. The signal produced by the coil further from the tape is subtracted from the signal produced by the coil closer to the tape; the difference being a signal caused by the additional flux produced by the crack. An alarm is sounded and in indicator lights when the signal is present.

8 Claims, 10 Drawing Figures

METHOD AND APPARATUS FOR MAGNETICALLY TESTING METAL TAPES

BACKGROUND OF THE INVENTION

This invention relates to apparatus and methods for detecting and locating faults or imperfections, such as cracks and fractures, in steel tapes and, particularly, perforated drive tapes, such as those used in elevator systems, generally known as selector tapes.

Selector tapes are employed in many elevator installations. The tape is constructed of ductile steel and is connected to the car as a continuous belt: one of its ends is attached to the top of the car and its other end is attached to the bottom. As the car ascends and decends in the hoistway, the tape drives a mechanical encoder which provides relative positional information as the car's location and movement in the shaft. The encoder is generally known as the selector. The selector tape usually contains perforations to mate with the teeth on a sprocket wheel that is rotated to drive the selector as the car ascends and decends. The perforations quite obviously provide reliable, positive mechanical connection to the selector to achieve precise, repeatable positional information. The tape is rather thin in order to give it a necessary level of ductility for it to loop smoothly around the sprocket.

Therefore, as the car moves within the elevator shaft, the selector tape is repeatedly bent and unbent or straightened as it moves around the sprocket to drive the selector. As a result, after extended service the tape can fatigue, which usually appears as small hairline cracks or fractures at first. If these are allowed to spread across the tape, a complete breakage can occur.

In very high buildings the selector tape can be several hundreds of feet long and, therefore, it is particularly prone to develop oscillations and thus continuously wiggle or sway in the elevator shaft. This can further accelerate tape fatigue. In addition, the tape's proneness to sway in tall buildings is increased by the tendency for tall buildings to sway in the wind. In fact, sometimes the swaying becomes so violent, as a result of car movement and building movement, that the tape strikes the cables connected to the car. This is a rare occurrence, however. In tall buildings tape fatigue therefore can develop more rapidly than in smaller buildings, where the tape is naturally much shorter.

If allowed to go uncorrected, tape fatigue can lead to complete tape breakage, in some cases, in which instance the car will be without any positive positional information, simply because the encoder or selector would not be driven. In the typical elevator installation, however, there are backup safety devices which prevent further car movement, except possibly to a near floor, in the event of complete breakage. Clearly, however, it is completely undesirable to allow tape fatigue to advance, unnoticed, to the point where complete breakage can occur. The only way to avoid that is to detect or diagnose fatigue in its early stages so that the tape can be repaired or replaced. Tape repair generally involves splicing in a new section into the tape. The detection procedure most commonly used consists simply of running the elevator up and down while a service technician holds his fingernail on the tape in order to detect the rough edge of a crack. Clearly this is a less than desirable procedure, particularly since it is slow and uneconomical.

Wire cables and rope are also subject to fatigue, in the form of broken wires, for much the same reasons. A prior art technique for detecting broken wires is to induce magnetic flux in the rope and sense the flux radiating from the rope as a result of the broken wires. This involves moving the rope so that the flux intersects a magnetic pickup device which thereupon produces a signal indicating the presence of a broken wire.

Although this technique is acceptable for steel ropes, it has no utility with selector tapes simply because this technique cannot distinguish between perforations and cracks. In other words, the tape's perforations will appear to be cracks. Hence, this technique evidences the distinct need for a crack detection technique specifically suited for metal tapes and the like which contain spaced apart perforations.

SUMMARY OF THE INVENTION

Thus, the object of the present invention is to provide both an apparatus and method for detecting and locating imperfections in selector tapes used in elevator installations, although it will undoubtedly have application where similar tapes and the like are used and, thus, similar fault detection problems are encountered.

The present invention focuses on the fact that if magnetic flux is impressed in the metal selector tape it will radiate from the perforations and cracks because of the resulting air gaps; but since the perforations are larger than the cracks, the flux from the perforations radiates further from the tape. A crack, therefore, can be detected by comparing the flux pattern near the tape with the flux pattern at a distance where only the flux from the perforations is present. If a crack is not present, the pattern at both positions will be the same; but if a crack is present, there will be additional flux near the tape and the pattern at the two positions will be different.

In accordance with the present invention, the tape is magnetized at the portion being checked for a crack and the resultant flux pattern at two distances from the tape is sensed through the use of two coils; one near the tape, so as to sense the flux from the perforations and any cracks and the second, further from the tape, at a distance where it senses only the flux from the perforations. The tape is moved and the flux intersecting each coil produces a signal reflecting the flux pattern at its position. Thus, the first coil will produce a signal from its intersection with the flux from the perforations and also any cracks. The second coil, however, produces a signal exclusively from the flux from the perforations. The signal from the second coil is subtracted from the signal from the first coil and if there is no crack, there will be substantially complete cancellation because the patterns will be substantially the same. But if there is a crack, a cracked induced remainder signal will be left; that being the result of the flux produced by the crack. By sensing for the presence of this remainder signal, a crack can be located and fault detection indicating apparatus actuated.

A feature, according to an extension of the present invention, is to use several pairs of these coils, spaced at different points along the width of the tape. Each coil pair acts as an independent fault sensor or detector and thus it becomes possible not only to determine the presence of a fault, but also its location along the width of the tape, as indicated by the sensor that produces the crack induced remainder signal.

Other objects, benefits, applications and features of the invention will be obvious to those skilled in the art from the following detailed description and claims, wherein:

DETAILED DESCRIPTION

Figure 1:
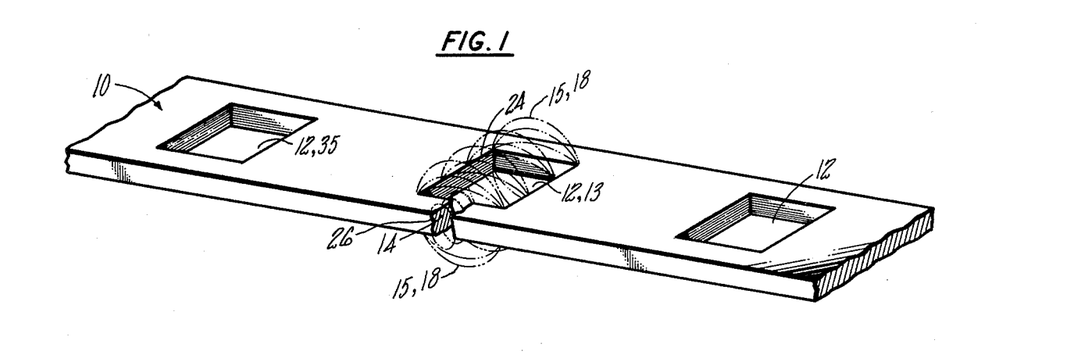
FIG. 1 is a perspective view of a typical selector tape.

In FIG. 1 a typical elevator selector tape 10 is shown which includes a plurality of evenly spaced apart perforations 12 that receive the teeth of a sprocketed wheel to drive the selector as the car moves. Neither the selector nor the sprocket are shown, however, since they are unrelated to an understanding of the present invention. Located in the sidewall of one perforation 13 there is a crack or break 14 which is intended to represent a possible imperfection in the tape detectable in accordance with the present invention. Quite obviously, the crack could appear in other portions of the tape, but this location is advantageous for describing the present invention.

Figure 2:
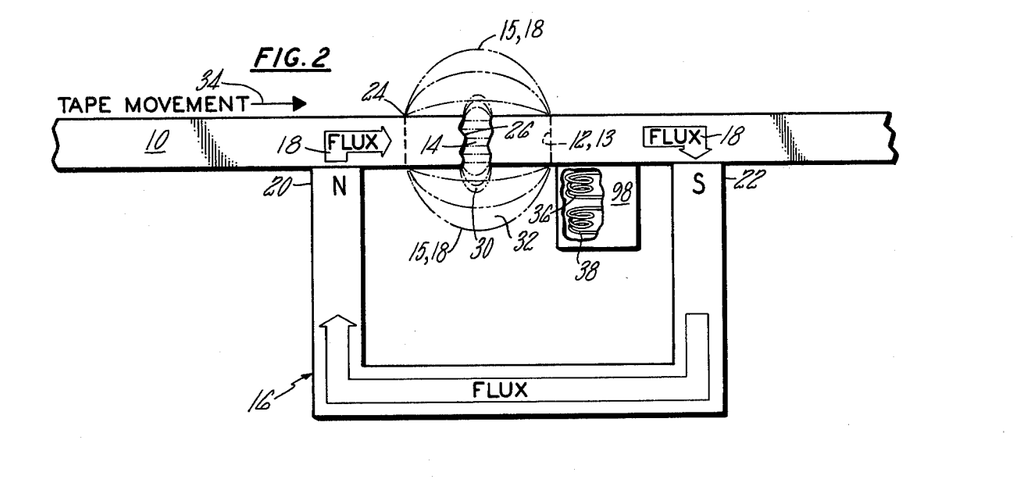
FIG. 2 is an illustration of the selector tape as it is tested for fault in accordance with the present invention.

With reference now to FIG. 2, in accordance with the present invention, a magnetic field is applied to the tape 10 by means of a permanent magnet 16 which is brought into close proximity to the tape surface. The tape is constructed of steel and, consequently, the field from the magnet induces magnetic flux 18 in the tape. The flux originates at the magnet's north pole 20 and enters the tape, where it is concentrated. However, at the perforation 13 and the crack 14 a portion 15 of the flux jumps the air gaps produced by the perforation and crack. The portion then reenters the tape and returns to the magnet's south pole 22. Hence, the tape is part of a continuous closed loop flux circuit wherein the magnet acts not unlike a voltage source in an electrical circuit in applying the field to the tape. Since the tape is constructed of steel it has very high permeability and therefore, it acts as a low impedance magnetic connection between the magnet's poles. In effect, it short-circuits the field and the flux that results is analogous to current flow. The air gaps, on the other hand, have extremely low permeability and, therefore, rather than acting as a "short circuit", act as a "quasi-high resistance", producing flux leakage, which appears as flux deconcentration across the air gaps. Consequently, as the flux 18 approaches an edge 24, 26 of the perforation and crack respectively, part of it radiates outwardly in a pattern, and part extends directly across the air gaps as shown in both FIGS. 1 and 2. It is important to note that the flux density varies directly with the size of the air gap; therefore, the flux density associated with the perforation is less than that of the crack. However, at a particular distance close to the tape, i.e. at point 30, the flux lines from the crack and perforation overlap. Therefore, at that position the flux density is greater than it is at a position further from the tape, i.e. at point 32, where the flux lines from the crack are not present.

Figure 3:
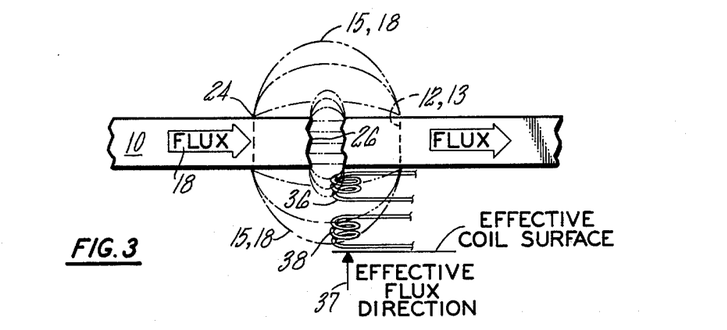
FIG. 3 is also an illustration of the selector tape as it is tested, the tape being in a moved position from the position in FIG. 2.

As mentioned previously, the tape is connected to the elevator car in a continuous loop and, in accordance with the present invention, to test the tape for the presence of the crack 14 the car is caused to move which, in turn, moves the tape in the direction of arrow 34, for example. If at the same time the magnet is held stationary, the externally radiating flux portions 15 can be envisioned to move with the tape, also in the same direction. As this happens, those perforations 12 successively behind perforation 13 (i.e. perforation 35) will be positioned between the magnet poles; a repetitive flux pattern is thus produced which moves from the north pole to the south pole in the direction of tape movement. Two magnetic flux pickups or sensors, coils 36 and 38, are located near the tape and as the tape moves, the radiating flux portions 15 intersect with these coils as shown in FIG. 3. The coil closest to the tape surface, coil 36, is intersected by the flux radiating from the perforation and the crack, whereas the coil further from the surface, coil 38, is positioned so as to be intersected only by the flux radiating from the perforation. This intersection produces an output voltage from each coil which is determined by the rate of change in flux density passing through the coil in a perpendicular direction 37 to the effective coil surface area.

Figure 4:
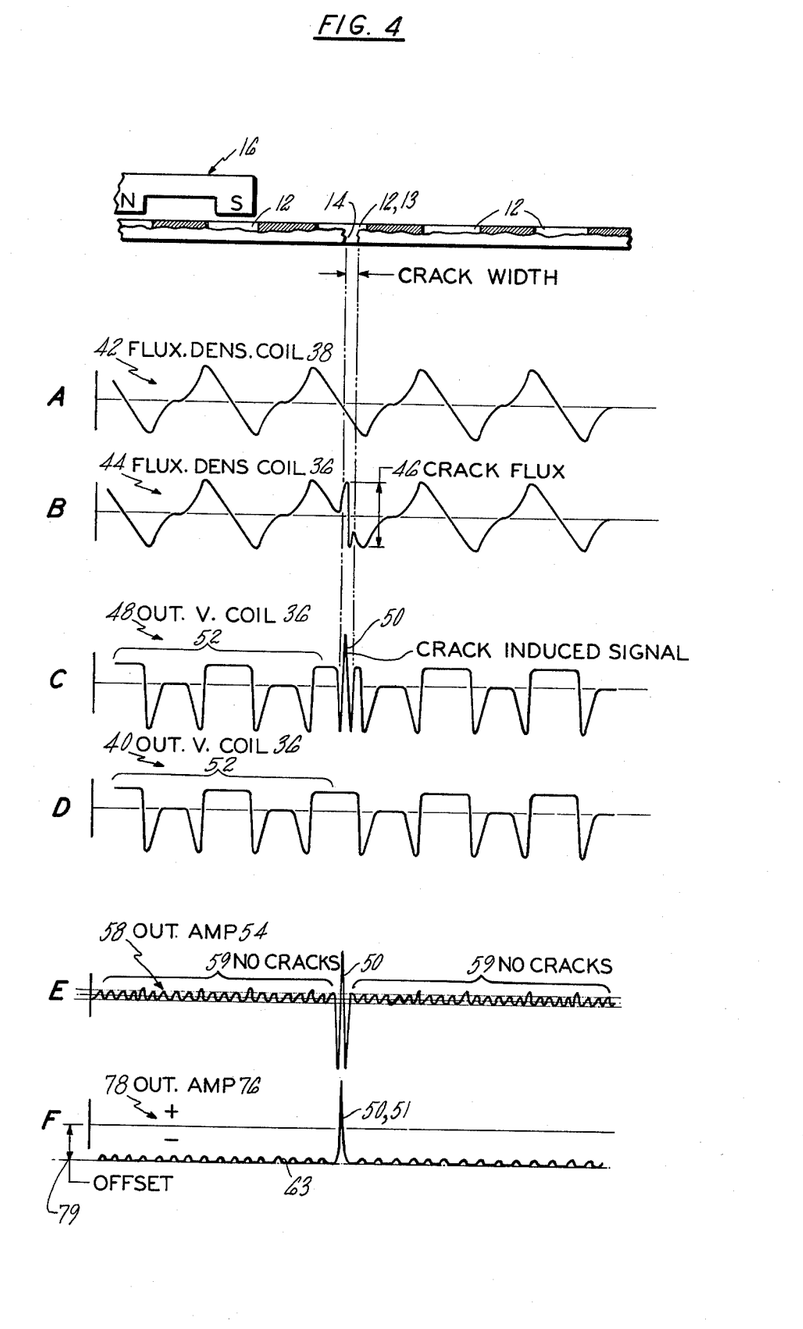
FIG. 4 is an illustration of waveforms, on a common time base, including the flux density at two distances from the tape and the output signals from the sensing coils.

The coil voltage is determined by this equation:

$V = N d\phi/dt$ $N$ = NUMBER OF COIL TURNS $\phi$ = EFFECTIVE FLUX DENSITY (PERPENDICULAR TO COIL SURFACE)·COIL AREA/TURN FIG. 4 contains waveforms showing the effective flux density produced by the perforations and the crack as the tape moves and the resulting coil output voltages. For example, an output voltage 40 (waveform D in FIG. 4) is produced across the terminals of the coil 38 which is a function of the slope of the flux density 42 (waveform A) that intersects the coil in the direction of arrow 37 as the tape moves. The periodic shape of the flux density is directly related to the fact that at the position of the coil 38 only that flux derived from the perforations 12 is encountered; there is no additional flux produced by the crack. On the other hand, the flux density 44 (waveform B) intersecting the coil 36 includes an additional superimposed flux density component 46, which is produced by the crack 14. The extent (width) of the component 46 is determined, of course, by the width of the crack. As a result, the output voltage 48 (waveform C) from the coil 36 is also periodic, like the output 40 of the coil 38, except that is, for an additional pulse 50, which is caused by the superimposed flux component 46. The magnitude of this additional pulse is determined in the same way, according to the foregoing equation: essentially from the slope of the superimposed flux density produced by the crack. Hence, the main distinction between the two output signals from the coils 36, 38 is the additional pulse 50; except for that, the output signals from both coils are identical and in phase. As described hereinafter, the output signal 40, from the coil 38, is subtracted from the output signal 48, from the coil 36, in order to remove all of the signal components except the additional signal 50. Therefore, it is advantageous that the coil windings be in a ratio which will produce equal signal levels for the common waveform components, i.e. pulses 52, so that when the output signal is subtracted virtually complete cancellation of the common components will occur. For the same reason, the coils are positioned relative each other to produce in phase signals, as shown in the waveforms.

Figure 5:
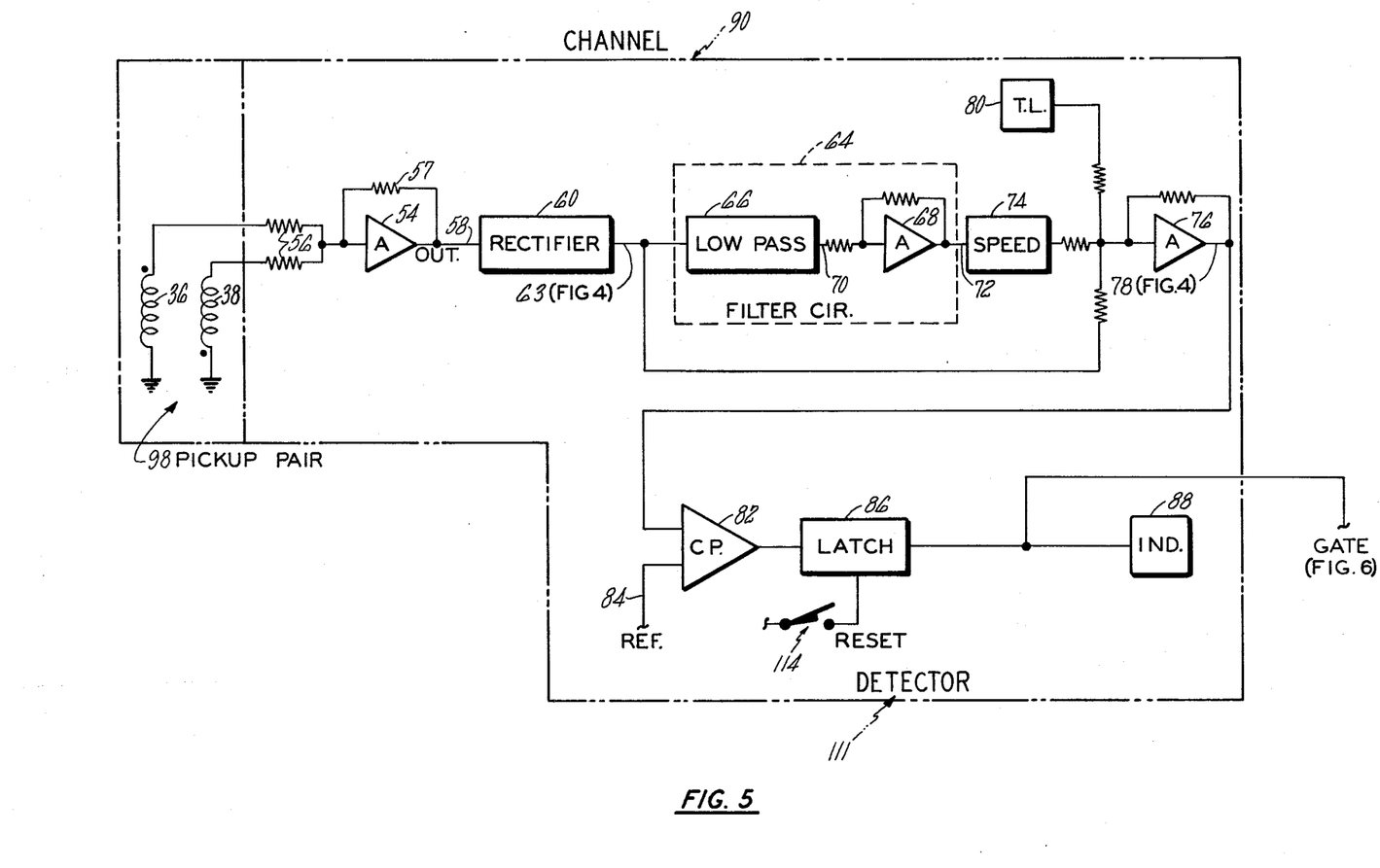
FIG. 5 is a block diagram of a detection apparatus according to the present invention.

Referring to FIG. 5, the output signals from the coil 38 is subtracted from the output signal from the coil 36 by connecting the two coils 36, 38 to a high gain feedback amplifier 54 in a phase reverse connection. The coils are coupled to the input of a closed loop amplifier 54 through coil isolation and current resistors 56. The amplifier's input is at virtual ground and the current from each coil flows through the feedback resistor 57. Thus, what appears on the output of the amplifier 54 is an output signal 58 (waveform E), which is the difference between signal 48 and signal 40. A complete cancellation of the common components of each signal (i.e. portions 52) does not occur, however, due to unavoidable coil output variations. Therefore, there is a residual background noise signal 59 which is indicative of the signals representing the other tape perforations which do not contain a crack.

The output signal from the amplifier 54 is supplied to a rectifier circuit 60 which removes the negative components to produce a rectified output signal 63 (in waveform F) which is supplied to a filter circuit 64, containing a passive, low pass filter 66 and a D.C. amplifier 68. The low pass filter 66 averages out the rectifier output to produce a D.C. signal at its output 70. The crack induced pulse 50 is of extremely short duration compared to the noise 59 and therefore does not alter the D.C. output from the filter 66. Consequently, the D.C. output produced from the L.P. filter 66 represents the flux condition associated with the perforations 12. In other words, the D.C. output from the L.P. filter is a function of the combined output from the coils 36, 38 when there is no break or crack in the tape and thus represents the flux condition when there is no crack or break. The D.C. signal from the L.P. filter is supplied to an amplifier 63 where it is increased and inverted at the amplifier output 72. The inverted D.C. signal is supplied through an adjustable speed bias control circuit 74 (an attenuator) to a second amplifier 76 where it is summed with the output from the rectifier 60. The result is an amplifier output signal 78 (waveform F) comprising the rectifier output 63 offset into the negative region which only goes positive when the crack induced signal portion 50 exceeds the offset voltage 79 (waveform F). The offset voltage is the sum of the output from the speed bias circuit 74 and an additional D.C. signal supplied from an adjustable threshold circuit 80. The purpose of the threshold circuit is to adjust the offset voltage so that penetration by the signal 50 is achieved. The speed bias circuit, in a similar manner, adjusts the offset voltage to reflect the change in the D.C. level produced by the filter 66 when the tape is moved at different speeds. The reason for this is simply that at different tape speeds the rate of change in flux in each coil will vary. Thus, from the foregoing equation, the magnitude of the rectified crack pulse 51 and the noise 52 (representing a "no break" condition) will also vary. The speed bias circuit consequently provides a means for compensating for these variations so that only pulses 50 of a magnitude greater than the threshold level will be positive.

The output from the amplifier 76 is supplied to a comparator 82 which fires when the crack induced signal 50 exceeds a reference voltage 84. Firing of the comparator actuates a latch 86 which powers an indicator 88 to provide notification to the user that a crack has been detected.

Figure 6:
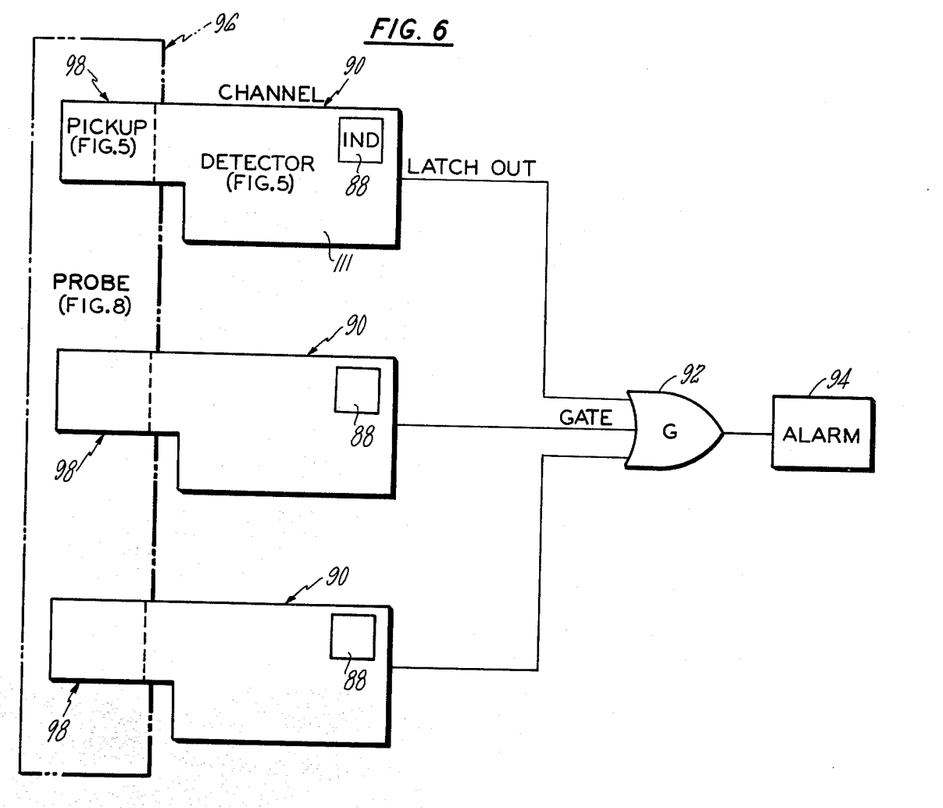
FIG. 6 is a block diagram of an alarm apparatus activated by the detection apparatus shown in FIG. 5.
Figure 7:
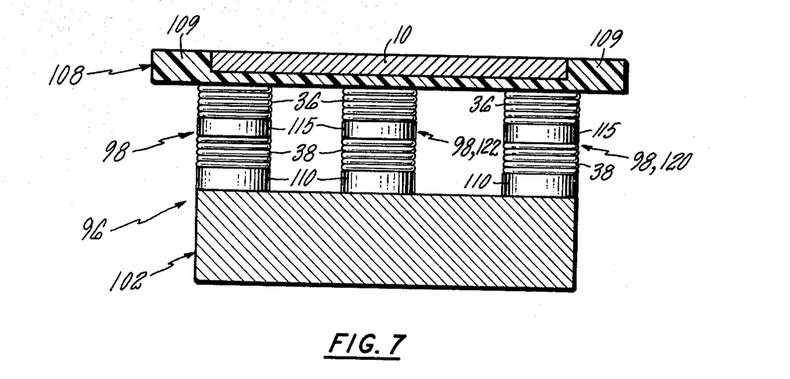
FIG. 7 is a sectional view, along the line 7—7 in FIG. 8, of a probe which can be used with the detection apparatus of FIG. 7 wherein a selector tape is positioned against the probe for testing.

Referring to FIG. 6, an extension of the present invention is to use three independent detector units or channels 90, each containing a pair 98 of the coils 36, 38 to detect a crack in the manner previously described. The coils 36, 38 associated with each channel are positioned at different points along the width of the tape, as shown in FIG. 7. Thus, each pair looks at a different portion of the tape. The output from the latch 86 in each unit is supplied to a gate 92, which activates an alarm 94, such as a horn or bell, when the latch is activated when a crack is detected. At the same time the indicator 88 associated with each channel will light indicating the location of the crack (middle or sides).

Figure 8:
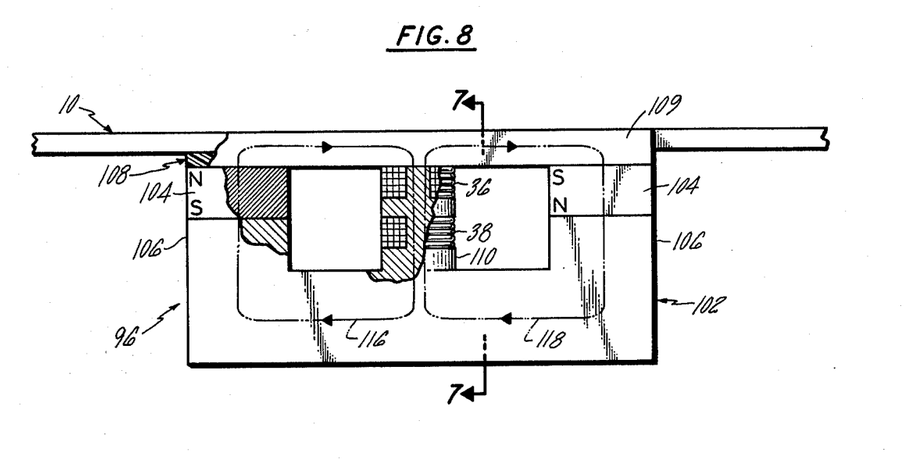
FIG. 8 is a composite elevation and cutaway view of the probe and tape in FIG. 7.
Figure 10:
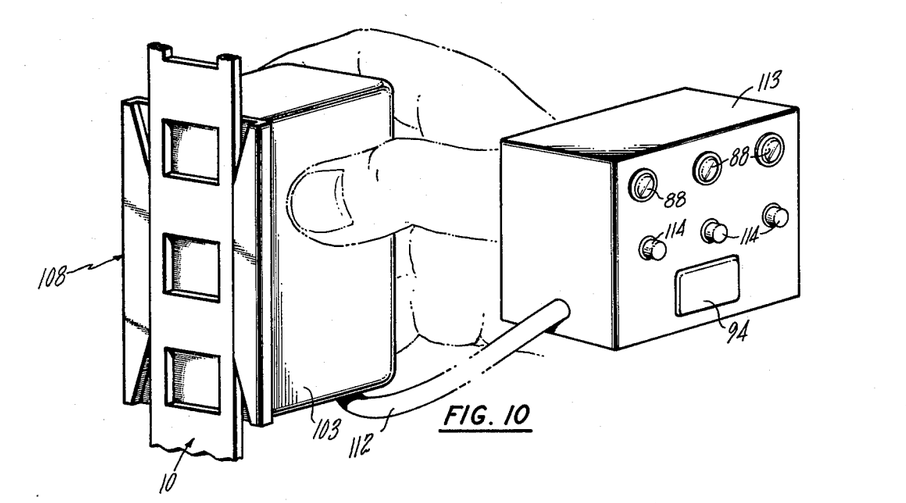
FIG. 10 is an illustration of a complete fault detection apparatus, according to the present invention, utilizing the probe of FIGS. 7-9.

In FIGS. 7 and 8, a convenient probe assembly 96 is shown which utilizes three coil pairs 98, each containing the coils 36, 38, to provide aforementioned three-channel detection. Each of the coil pairs 98 is mounted on a common high permeability core 110 which is part of a larger magnetic frame 102. On the ends of the magnetic frame there are two permanent magnets 104 with opposite poles facing the tape. As a result, the entire frame, in effect, is magnetized and becomes a permanent magnet with its legs 106 having opposite polarities, as shown. A nonmetallic, low friction (i.e. polyethylene) separator-guide plate 108 is fastened on the frame. The pull of the magnets on the tape holds it in a flattened position in a tappered slot or groove (defined by walls 109) in the plate as it is moved during testing. As illustrated in FIG. 10, the frame is protected in a shell 103 and the tape is tested simply by handholding the probe (grasping the shell) while the tape is moved. The probe can also be moved, back and forth, to home in on a crack. The output signals from the coils are transmitted over a multiconductor cable 112 to their respective detectors 111 (FIG. 5) in a container 113 with the alarm 94, indicator lamps 88 and latch reset controls 114 conveniently located on the front. The entire apparatus is battery powered and hence, is portable for convenient field service applications.

Figure 9:
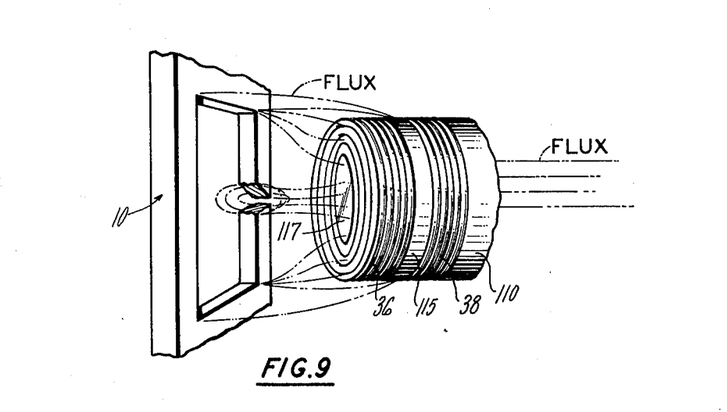
FIG. 9 is an illustration showing the operation of a coil pair included in the probe when detecting a crack in the tape.

The coils 36, 38 are wound in a high permeability core 110. The inner coil 36 is separated from the outer coil 38 by a flanged portion 115 of the core. Referring to FIG. 9, as a result, when a perforation or crack passes near the core the flux is drawn into it. After it enters the core it returns through the remainder of the frame to the magnet poles on the frame legs to complete the flux circuit. The surface area of the flange portion, however, is greater than the surface area of the narrower portion 117 and thus it gathers more flux into the outer coil. This combined with the outer coil's position at a distance where the crack flux is not present enhances its restricted sensing function: to sensing only the perforation flux. Conversely, the small "viewing area" of the inner coil, because of its small core, and its position near the tape enables it to sense the flux from both the perforation and slots. In addition, with both coils wound on the same core, the coil output signals will be in phase, which is preferred for proper operation, as suggested earlier.

Operation of the probe does not depart to any significant extent, however, from the earlier description operation of the model apparatus illustrated in FIGS. 1-6 which employs air coils. The most apparent distinction lies in the use of the three coil pairs in order to view small areas of the tape, a feature which is clearly enhanced by the restricted viewing angle of each inner coil 36 that arises from the unique core structure. Another distinction is that the "air" coils 36, 38 in FIG. 2 simply intersect the flux lines from the crack and slot in free space, but utilizing the probe assembly, the core attracts and diverts the flux back into the magnetic frame where it returns to the proper magnet pole, as illustrated in FIG. 8. In other words, the core upon which the coils are wound is a common branch of two closed loop parallel flux circuits 116, 118; each including one of the magnets mounted on the frame as its flux source.

The coil pickup pairs 98 associated with each of the three channels 90 looks at a portion of the tape, along its width, although the detection area for the channels overlap somewhat. If a crack passes by the pickups as the tape is moved, it will be detected in at least one of the channels, which will cause the alarm to sound and the indicator associated with that channel to light. Thus, the service technician will know that a crack has passed by and by the light he will know where it is along the tape's width. For example, if there is a small crack in the right side of the tape, it would be detected by the coil pair 120. If the crack extended to the middle of the tape, it would also be detected by the middle channel 122; then the corresponding two indicators 88 would light (the right and middle). Once a crack is spotted, the service technician stops the elevator car and if necessary resets the latches and backs the car up or preferably moves the probe in order to "home in" on the crack. Car speed and therefore tape speed can vary. Therefore, the output signals from the pickup coils can also vary since the rate of change in flux ($d\phi/dt$) is directly proportional to tape speed. The outputs can vary also because of different tape structures; for example, fewer perforations or differently shaped perforations, depending upon the installation. The speed bias control permits system adjustment for these variations. When using the apparatus the service technician adjusts the speed bias control in order to adjust the offset voltage level (which reflects only the signals from the perforations) so that audible and visual indications are produced only by the cracks.

Thus, the apparatus and method according to the invention can be used to detect faults in other metal tape-like devices wherein similar detection problems are confronted. Moreover, the foregoing will undoubtedly suggest and teach to one skilled in the art possible modifications and variations of the present invention nevertheless embracing its true scope and spirit. The claims that follow, therefore, are intended to embrace all such modifications and variations.

I claim:

1. Apparatus for testing slotted, magnetizable metal tapes to locate cracks therein, comprising:
    means for magnetizing a section of the tape,
    means for sensing magnetic flux which radiates from cracks and slots in the tape,
    means for providing an indication of the presence of the crack, in a portion of the tape, in response to an output signal, provided by said sensing means, characterized by:
    said sensing means comprising means for simultaneously sensing, at two positions at different distances from the tape surface, flux radiating from the tape, and providing, for each position, a signal which reflects the sensed flux; means for summing said signals so as to remove components that are common to each signal for providing a difference signal comprising substantially the components caused by the flux from a crack; and means for deriving a signal representing the average level of said difference signal and for summing said average level signal with said difference signal and predetermined threshold for providing a crack identification signal comprising substantially a signal component caused by the flux from the crack; and
    said means for providing an indication of the presence of a crack comprising means for comparing said crack identification signal with a predetermined reference signal, and resetable means, operable in response to an output signal from said comparing means for operating an indicator device, such as a light or alarm or both.

2. An apparatus according to claim 1, characterized in that:
    said sensing means comprises a pair of magnetic pickup coils; one of the coils being closer to the tape surface than the other; both of said coils being oriented on the same axis which is substantially normal to the tape surface; said coils being separated by a magnetic separator which increases the flux sensing area of the coil further from the tape.

3. An apparatus according to claim 1, characterized by: a plurality of channels, each for sensing a portion of the tape along the width for providing, for said portion, a crack identification signal and an indication of a crack therein; each channel comprising said sensing means and said means for providing an indication of the presence of a crack.

4. An apparatus according to claim 1, characterized in that said means for magnetizing the tape is adapted for establishing unidirectional, substantially constant flux in the tape as the tape is moved relative to said means and vice versa.

5. An apparatus according to claim 1, characterized in that said sensing means comprises:
    a rectification circuit for providing a unipolar output signal from said difference signal;
    a low pass filter for providing an output signal from the unipolar output signal, said low pass filter output signal having a polarity which is opposite that of the unipolar output signal; and
    an amplifier circuit for providing an output signal which comprises the sum of the output signal from the rectification circuit, the filter circuit, and an adjustable threshold signal.

6. A method for testing magnetizable metal tapes, characterized by:
    establishing a unidirectional, substantially constant magnetic flux in the tape;
    moving the tape relative to a flux sensing apparatus and vice versa;
    providing a first signal from the flux at a first position from the tape surface;

providing a second signal from the flux at a second position, further from the tape than said first position;

providing a crack identification signal, by subtracting the first signal from the second, to provide a net composite signal, rectifying said composite signal, to provide a unipolar composite signal, filtering the unipolar signal to provide an average signal, and subtracting the average from the unipolar composite signal; and providing an alarm if the crack identification signal exceeds a predetermined threshold.

7. A method according to claim 6, characterized in that:
first and second signals are provided for a plurality of positions across the tape; and
a crack identification is provided for each pair of said signals.

8. A method according to claim 6, characterized in that:
the first signal is provided by intercepting the flux within a first area;
the second signal is provided by intercepting the flux in a second area; and
said first area is smaller than said second area.

* * * * *

UNITED STATES PATENT AND TRADEMARK OFFICE
CERTIFICATE OF CORRECTION

PATENT NO. : 4,270,088
DATED : May 26, 1981
INVENTOR(S) : Herbert R. Weischedel

It is certified that error appears in the above—identified patent and that said Letters Patent is hereby corrected as shown below:

Claim 6, column 9, line 9, "subtracting the average from" should read --subtracting the average signal from--.

Signed and Sealed this

Thirty-first Day of August 1982

[SEAL]

Attest:

GERALD J. MOSSINGHOFF

Attesting Officer     Commissioner of Patents and Trademarks